United States Patent [19]

Eastland et al.

[11] Patent Number: 5,406,004
[45] Date of Patent: Apr. 11, 1995

[54] HYDROGENATION PROCESS FOR THE PREPARATION OF ALCOHOLS AND DIOLS UTILIZING GAS AND LIQUID PHASES

[75] Inventors: Philip H. D. Eastland, Teddington; John Scarlett, Spennymoor; Michael W. M. Tuck, London; Michael A. Wood, Middlesbrough, all of England

[73] Assignee: Eastman Chemical Company, Kingsport, Tenn.

[21] Appl. No.: 175,546

[22] Filed: Dec. 30, 1993

[30] Foreign Application Priority Data

Dec. 2, 1993 [GB] United Kingdom ................ 9324782

[51] Int. Cl.$^6$ .............................................. C07C 31/13
[52] U.S. Cl. .................... 568/831; 568/822; 568/830; 568/840; 568/834; 568/861; 568/864; 568/881
[58] Field of Search ............... 568/822, 830, 831, 840, 568/861, 864, 881, 834; 570/206

[56] References Cited

U.S. PATENT DOCUMENTS

| | | | |
|---|---|---|---|
| 2,040,944 | 5/1936 | Lazier | 568/864 |
| 2,079,414 | 5/1937 | Lazier | 568/864 |
| 2,091,800 | 8/1937 | Adkins et al. | 568/864 |
| 2,105,664 | 1/1938 | Lazier | 568/864 |
| 2,137,407 | 11/1938 | Lazier | 568/831 |
| 2,755,317 | 7/1956 | Kassel | |
| 2,818,393 | 12/1957 | Lefrancois et al. | |
| 2,830,095 | 4/1958 | Nicolaisen | 570/206 |
| 2,884,450 | 4/1959 | Holmquist | 568/831 |
| 2,901,466 | 8/1959 | Kibler et al. | 568/864 |
| 2,917,549 | 12/1959 | Hasek et al. | 568/831 |

(List continued on next page.)

FOREIGN PATENT DOCUMENTS 143634 6/1985 European Pat. Off. .
(List continued on next page.)

OTHER PUBLICATIONS

Mansour et al., "Sel. Hydrog. of Esters to Alcoh. with Catal. Obtained Rh$_2$O$_3$, Sn (n-C$_4$H$_9$)$_4$ and SiO$_2$ and Based On Isol. Active Centres", *Angew. Chem.* 101. (1989) Nr. 3, 360–63.
Wehner & Gustafson, "Catalytic Hydrog. of Esters Over Pd/ZnO", *Journ. of Catalysis,* 135, 420–426 (1992).
Homer Adkins, "Catal. Hydrog. of Esters to Alcoh.", *Organic Reactions,* vol. 8, Chp. 1, pp. 2–27 (1954).

*Primary Examiner*—Werren B. Lone
*Attorney, Agent, or Firm*—J. Frederick Thomsen; Harry J. Gwinnell

[57] ABSTRACT

A process is described for the production of a hydroxylic compound selected from alcohols and diols by hydrogenation of a corresponding hydrogenatable material selected from monoesters of carboxylic acids, monoesters of dicarboxylic acids, diesters of dicarboxylic acids, lactones, and mixtures of two or more thereof which comprises:

(a) providing a hydrogenation zone containing a charge of a granular heterogeneous ester hydrogenation catalyst;

(b) supplying to the hydrogenation zone a vaporous feed stream containing hydrogen and a hydrogenatable material selected from monoesters of carboxylic acids, monoesters of dicarboxylic acids, diesters of dicarboxylic acids, lactones, and mixtures of two or more thereof, at an inlet temperature which is above the dew point of the mixture;

(c) maintaining the hydrogenation zone under temperature and pressure conditions which are conducive to effecting hydrogenation of esters;

(d) recovering from the hydrogenation zone a two phase product stream containing a hydroxylic compound selected from alcohols and diols at an exit temperature which is below its dew point.

In a preferred process the hydrogenatable material comprises dimethyl cyclohexanedicarboxylate.

18 Claims, 1 Drawing Sheet

U.S. PATENT DOCUMENTS

| | | | |
|---|---|---|---|
| 3,334,149 | 8/1967 | Akin et al. | 568/831 |
| 4,032,458 | 6/1977 | Cooley et al. | 568/864 |
| 4,052,467 | 10/1977 | Mills et al. | 568/881 |
| 4,172,961 | 10/1979 | Henery et al. | 568/864 |
| 4,268,695 | 5/1981 | Lange et al. | 568/864 |
| 4,361,710 | 11/1982 | Weitz et al. | 568/864 |
| 4,584,419 | 4/1986 | Sharif et al. | 568/864 |
| 4,652,685 | 5/1987 | Cawse et al. | 568/831 |
| 4,751,334 | 6/1988 | Turner et al. | 568/864 |
| 4,837,368 | 6/1989 | Gustafson et al. | 568/881 |
| 4,918,248 | 4/1990 | Hattori et al. | 568/885 |
| 4,929,777 | 5/1990 | Irick, Jr. et al. | 568/864 |
| 4,999,090 | 3/1991 | Tateno et al. | 568/822 |
| 5,030,771 | 7/1991 | Fuhrmann et al. | 568/831 |
| 5,124,435 | 6/1992 | Mori et al. | 528/307 |
| 5,142,067 | 8/1992 | Wegman et al. | 546/326 |
| 5,185,476 | 2/1993 | Gustafson | 568/831 |
| 5,191,091 | 3/1993 | Wegman et al. | 549/326 |

FOREIGN PATENT DOCUMENTS

| | | |
|---|---|---|
| 241760 | 10/1987 | European Pat. Off. . |
| 301853 | 2/1989 | European Pat. Off. . |
| 353990 | 2/1990 | European Pat. Off. . |
| 378756 | 7/1990 | European Pat. Off. . |
| 552463 | 7/1993 | European Pat. Off. . |
| 1276722 | 10/1961 | France . |
| 1144703 | 3/1963 | Germany . |
| 1159925 | 12/1963 | Germany . |
| 2719867 | 11/1978 | Germany . |
| 3843956 | 6/1990 | Germany . |
| 4141199 | 6/1993 | Germany . |
| 988316 | 4/1965 | United Kingdom . |
| 1024318 | 3/1966 | United Kingdom . |
| 1454440 | 11/1976 | United Kingdom . |
| 1464263 | 2/1977 | United Kingdom . |
| 2116552 | 9/1985 | United Kingdom . |
| 2250287 | 6/1992 | United Kingdom . |
| 8203854 | 11/1982 | WIPO . |
| 86/03189 | 6/1986 | WIPO . |
| 86/07358 | 12/1986 | WIPO . |
| 88/00937 | 2/1988 | WIPO . |
| 89/00886 | 2/1989 | WIPO . |
| 90/08121 | 7/1990 | WIPO . |
| 91/01961 | 2/1991 | WIPO . |

HYDROGENATION PROCESS FOR THE PREPARATION OF ALCOHOLS AND DIOLS UTILIZING GAS AND LIQUID PHASES

FIELD OF THE INVENTION

This invention relates to a process for the production of a hydroxylic compound selected from alcohols and diols by hydrogenation of a corresponding hydrogenatable material selected from monoesters of carboxylic acids, monoesters of dicarboxylic acids, diesters of dicarboxylic acids, and mixtures of two or more thereof.

BACKGROUND OF THE INVENTION

It is known to produce alcohols by hydrogenation, or more properly hydrogenolysis, of monoesters of carboxylic acids. The reaction can be summarised as follows:

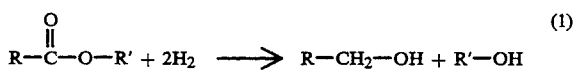  (1)

In the book "Catalytic Hydrogenation" by M. Freifelder, published by John Wiley and Sons Inc. (1978), it is stated at page 129 et seq. that the catalyst of choice is barium promoted copper chromite. In "Organic Reactions", Vol. 8, published by John Wiley and Sons Inc. (1954), Chapter I is by Homer Adkins and is entitled "Catalytic Hydrogenation of Esters to Alcohols". It is suggested that a "copper chromite" catalyst is more correctly described as an approximately equimolar combination of cupric oxide and cupric chromite, i.e. $CuO,CuCr_2O_4$. Reference may also be had to Kirk-Othmer's "Encyclopedia of Chemical Technology" (Third Edition), Volume 1, page 733 to 739.

Patent specifications describing hydrogenation of esters to yield alcohols include US-A-2040944, US-A-2019414, US-A-2091800, and FR-A-1276722.

It is known to effect hydrogenation of certain esters and diesters in the vapour phase. For example it has been proposed to use a reduced copper oxide/zinc oxide catalyst for effecting hydrogenation of esters in the vapour phase. In this connection attention is directed to GB-B-2116552. Also of relevance is WO-A-90/8121.

It is further known to produce diols, such as butane-1,4-diol, by catalytic hydrogenation of esters of dicarboxylic acids, such as a dimethyl or diethyl ester of maleic acid, fumaric acid, succinic acid, or a mixture of two or more thereof. Such processes are described, for example, in GB-A-1454440, GB-A-1464263, DE-A-2719867, US-A-4032458, and US-A-4172961.

Production of butane-1,4-diol by vapour phase hydrogenation of a diester, typically a dialkyl ester, of a $C_4$ dicarboxylic acid selected from maleic acid, fumaric acid, succinic acid, and a mixture of two or more thereof has been proposed. In such a process the diester is conveniently a di-($C_1$ to $C_4$ alkyl) ester, such as dimethyl or diethyl maleate, fumarate, or succinate. A further description of such a process can be found in US-A-4584419, EP-A-0143634, WO-A-86/03189, WO-A-86/07358, and WO-A88/00937.

In all of the above-mentioned vapour phase processes the esters or diesters all have a vapour pressure which is high compared to the vapour pressure of dimethyl 1,4-cyclohexanedicarboxylate and 1,4-cyclohexanedimethanol.

Another commercially important diol is 1,4-cyclohexanedimethanol. This compound is used to prepare highly polymeric linear condensation polymers by reaction with terephthalic acid and is useful as an intermediate in the preparation of certain polyester and polyester amides. The use of 1,4-cyclohexanedimethanol for such purposes is disclosed in, for example, US-A-2901466. This document teaches that the trans-isomer of polycyclohexylenedimethylene terephthalate has a higher melting point range (315°-320° C.) than the corresponding cis-isomer (260°-267° C.).

One method for preparing 1,4-cyclohexanedimethanol (hexahydroterephthalyl alcohol) involves the hydrogenation of diethyl 1,4-cyclohexanedicarboxylate (diethyl hexahydroterephthalate) in a slurry phase reactor in the presence of a copper chromite catalyst at a pressure of 3000 psia (about 206.84 bar) and a temperature of 255° C., as is described in Example 3 of US-A-2105664. The yield is said to be 77.5%.

The hydrogenation of dimethyl 1,4-cyclohexanedicarboxylate (DMCD) to 1,4-cyclohexanedimethanol (CHDM) is shown below in equation (1):

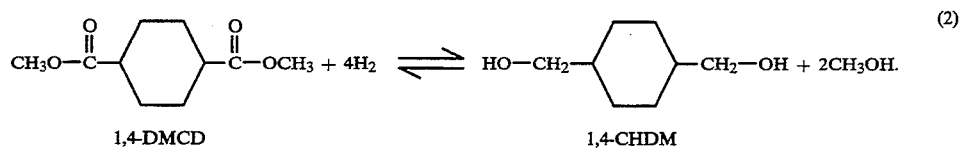

1,4-DMCD                    1,4-CHDM    (2)

Several processes for the production of 1,4-cyclohexanedimethanol and related alcohols have been published since the issuance of US-A-2105664 in 1938. These processes have, almost exclusively, focused on methods for performing the above hydrogenation reaction in the liquid phase. Advances have been reported in the general areas of cis-/trans- isomer selectivity (US-A-2917549, GB-A-988316 and US-A-4999090), catalyst type (GB-A-988316 and US-A3334149) and conditions of plant operation (US-A-5030771).

In the hydrogenation of dimethyl 1,4-cyclohexanedicarboxylate the two geometrical isomers of CHDM produced are:

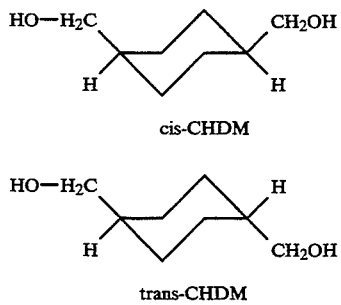

The resulting 1,4-cyclohexanedimethanol product is a mixture of these two isomers which have different melting points. As reported on page 9 of the book "Fiber Chemistry" edited by Menachem Lewis and Eli M. Pearce, published by Marcel Dekker, Inc.: "Both the alicyclic ester [i.e. dimethyl 1,4-cyclohexanedicarboxylate] and the alicyclic diol [i.e. 1,4-cyclohexanedimethanol] exist in two isomeric forms, cis . . . and trans . . . , that are not interconvertible without bond rupture". The passage continues later: "Control of the [cis-:trans-] ratio is important [in 1,4-cyclohexanedimethanol] since many polymer and fiber properties depend on it".

The cis-isomer of 1,4-cyclohexanedimethanol has a melting point of 43° C. and the trans has a melting point of 67° C. The higher melting point trans-isomer is often preferred over the cis-isomer for use as a reagent in the preparation of polyester and polyester-amides if a high melting point for such materials is considered desirable. As noted above, the trans-isomer of a typical polyester, such as trans-polycyclohexylmethyl terephthalate, has a higher melting point than the cis-isomer. Hence, for example, US-A-5124435 discloses a polyester copolymer, the 1,4-cyclohexanedimethanol content of which has a trans-isomer content of at least 80 mole %, and which has a high heat resistance. The preferment of trans-1,4-cyclohexanedimethanol over cis-1,4-cyclohexanedimethanol is also discussed in US-A-2917549, in US-A-4999090 and in GB-A988316.

A liquid phase process for the production of 1,4-cyclohexanedimethanol by plural stage hydrogenation of dimethyl terephthalate is described in US-A-3334149. This utilises a palladium catalyst to effect hydrogenation of dimethyl terephthalate to dimethyl 1,4-cyclohexanedicarboxylate, followed by use of a copper chromite catalyst in the liquid phase to catalyse the hydrogenation of that diester to 1,4-cyclohexanedimethanol. In the procedure described in Example 1 of that patent specification a residence time of about 40 to 50 minutes is used in the second stage of this process. The activity of the copper chromite catalysts recommended in US-A-3334149 is such that long residence times are required.

In a liquid phase process for the production of 1,4-cyclohexanedimethanol, such as is disclosed in US-A-3334149, the trans-:cis- isomer ratio of the product 1,4-cyclohexanedimethanol will tend towards an equilibrium value. This equilibrium value has been reported variously and may lie between about 2.57:1 (trans-:cis- 1,4-cyclohexanedimethanol) (as reported in GB-A-988316) and about 3:1 (as reported in US-A-2917549). However, the starting material, dimethyl 1,4-cyclohexanedicarboxylate, is generally commercially obtainable as a mixture of cis- and trans-isomers wherein there is a preponderance of the cis-isomer. Thus in a typical commercial grade of dimethyl 1,4-cyclohexanedicarboxylate the trans-:cis- isomer ratio is from about 0.5:1 to about 0.6:1.

Attempts to deal with the problem of the presence of an excess of the less desirable cis-1,4-cyclohexanedimethanol isomer in any process for 1,4-cyclohexanedimethanol manufacture have focused on the isomerisation of the cis-isomer of cyclohexanedimethanol to the trans-isomer thereof.

US-A-2917549 discloses a process for isomerising cis-1,4-cyclohexanedimethanol to trans-1,4-cyclohexanedimethanol which comprises heating cis-1,4-cyclohexanedimethanol at a temperature of at least 200° C. in the presence of an alkoxide of a lower atomic weight metal such as lithium, sodium, potassium, calcium or aluminium. However, the process of US-A-2917549 necessarily involves a two-stage process wherein the initial cis-/trans- 1,4-cyclohexanedimethanol hydrogenation product is recovered from the hydrogenation zone and subjected to temperatures in excess of 200° C. in the presence of a metal alkoxide catalyst under an atmosphere of nitrogen. The capital and operational costs associated with a plant designed to carry out the process taught in US-A-2917549 would be undesirably high. Another disadvantage of such a plant is the associated hazard relating to the use of metal alkoxides as catalysts in the isomerisation zone. Such catalysts are required to effect the isomerisation, which is reported not to occur under typical hydrogenation conditions using hydrogenation catalysts such as copper/chrome or Raney nickel catalysts, according to the teaching of Example 11 of US-A-2917549. Furthermore, steps would be required to prevent product contamination by the metal alkoxide catalyst.

US-A-4999090 discloses a process for the isomerisation of cis-1,4-cyclohexanedimethanol by distillation in the presence of an alkali metal hydroxide or alkoxide at a temperature of between 150° C. and 200° C. and at a pressure of between 1 mm Hg and 50 mm Hg (between 1.33 millibar and 66.5 millibar). This process has very similar disadvantages to those of US-A-2917549.

GB-A-988316 teaches a process for the preparation of trans-1,4-cyclohexanedimethanol in which a mixture of cis- and trans-isomers of dimethyl hexahydroterephthalate (i.e. dimethyl 1,4-cyclohexanedicarboxylate) is hydrogenated at elevated temperature and pressure in the presence of a Cu/Zn catalyst. Trans-1,4-dimethylolcyclohexane (i.e. trans-1,4-cyclohexanedimethanol) is separated by crystallisation from the reaction product and then the residual product, now enriched in cis-1,4-cyclohexanedimethanol, is recycled to the hydrogenation zone whereupon it undergoes isomerisation to a cis-/trans- 1,4-cyclohexanedimethanol mixture. The recycle procedure may be repeated to obtain a 1,4-cyclohexanedimethanol product containing the trans-isomer in substantial excess. However, the process according to GB-A-988316 is more preferably operated under conditions such that recycled cis-isomer enriched product is combined with fresh dimethyl 1,4-cyclohexanedicarboxylate feed on re-entry to the hydrogenation zone. The effectiveness of recycling the cis-isomer to the hydrogenation zone is largely a result of the dual function of the copper/zinc catalyst which possesses both a hydrogenating and an isomerising catalytic action. As would be expected from thermodynamic principles, the isomerising action is most effective when a mixture containing a preponderance of the cis-isomer is recycled to the hydrogenation zone. However, recycling the cis-isomer in this way is acknowledged to cause a new problem, that of the formation of unwanted by-products, such as 1-methyl-4-hydroxymethylcyclohexane, which may be formed by operating the hydrogenation reaction under too severe conditions. To minimise the formation of such by-products, the hydrogenation zone may be operated under "relatively mild conditions", according to the teaching of GB-A-988316 (see, for example page 2, lines 55 to 79 of GB-A-988316). However, such mild conditions reduce the achieved conversion of dimethyl 1,4-cyclohexanedicarboxylate with the result that, for any one pass through the hydrogenation zone, a significant quantity of dimethyl hexahydroterephthalate (dimethyl 1,4-cyclohexanedicarboxylate) remains unconverted. By the term "relatively mild conditions" is meant a temperature of at least 200° C., preferably between 240° C. and 300° C., and a pressure of 200 to 300 atmospheres (202.65 bar to 303.98 bar), according to page 2, lines 26 to 32 of GB-A-988316. The use of such high pressures at these elevated temperatures can be hazardous, besides requiring reactors with thick walls and flanges of special alloy constructed to withstand such extreme pressures. Hence it is expensive to construct a plant to operate at pressures as high as envisaged in GB-A-988316. Furthermore it is potentially hazardous to operate a plant operating at 200 atmospheres (202.65 bar) or above, as well as being very expensive, not only in terms of the capital cost of the plant but also with regard to operating costs. A substantial proportion of this capital cost is associated with the rigorous safety precautions that must be taken when operating a high pressure conventional commercial scale hydrogenation plant. It is also expensive to compress gaseous streams to such high pressures and to circulate them through the plant.

Although there is a passing reference (see page 1, line 84 of GB-A-988316) to use of "the gaseous phase", even at temperatures of 300° C. both cis- and trans- dimethyl hexahydroterephthalate would be in the liquid phase at pressures of 200 to 300 atmospheres (202.65 bar to 303.98 bar) at the hydrogen:ester ratio envisaged in the Examples. Thus in each of the Examples of GB-A-988316 liquid phase conditions are used. According to Example 4, which uses a feed mixture containing dimethyl hexahydroterephthalate (i.e. 1,4-dimethyl cyclohexanedicarboxylate), and methanol such as might be used in a recycling process, the isomers present in the diol in the hydrogenation product are stated to represent an equilibrium mixture of about 72% of the trans- and about 28% of the cis-isomer, i.e. a trans-:cis-ratio of about 2.57:1.

The hydrogenation of an ester, diester or lactone feedstock is generally an exothermic reaction. In a liquid phase reaction the feedstock is normally diluted with an inert diluent, conveniently with recycled product hydroxylic compound, and the catalyst is wholly wetted with liquid. The diluent acts as a heat sink and helps to prevent the danger of damage to the catalyst due to the exothermic nature of the hydrogenation reaction.

In a typical vapour phase hydrogenation process the unsaturated organic compound, i.e. the ester, diester or lactone, is normally vaporised directly into a hot hydrogen-containing gas to give a vaporous mixture, which may be heated further or diluted with more hot hydrogen-containing gas in order to raise its temperature above the dew point. It is normally essential to ensure that the vaporous mixture in contact with the catalyst is above its dew point, i.e. above that temperature at which a mixture of gases and vapour just deposits liquid as a fog or a film. This dew point liquid will normally contain all the condensable components of the vapour phase, as well as dissolved gases, in concentrations that satisfy the usual vapour/liquid criteria. It may include the starting material, an intermediate product, a by-product and/or the final hydrogenation product. Generally the process is operated so that the temperature of the vaporous feed mixture is above its dew point, for example about 5° C. to about 10° C. above its dew point. Moreover it is desirable to prevent contact of droplets of liquid with the catalyst, particularly droplets which are rich in the unsaturated organic compound, because damage to the catalyst may result from loss of mechanical strength, from formation of hot spots on the surface of the catalyst or in the pores of the catalyst, due to the exothermic nature of the reaction, leading possibly to sintering and thereby to loss of chemically effective catalyst surface area (particularly in the case of copper-containing catalysts), or from disintegration of the catalyst pellets possibly as a result of explosive vaporisation within the pores of the pellets.

SUMMARY OF THE INVENTION

It is accordingly an object of the present invention to provide a process for the production of a hydroxylic compound selected from alcohols and diols by hydrogenation of a corresponding hydrogenatable material selected from monoesters of carboxylic acids, monoesters of dicarboxylic acids, diesters of dicarboxylic acids, lactones, and mixtures of two or more thereof which can be operated with substantially increased safety and operating economy at relatively low pressures. Another object of the invention is to provide a process for production of cyclohexanedimethanol by hydrogenation of dimethyl cyclohexanedicarboxylate wherein the hydrogenation step yields directly a cyclohexanedimethanol product with a higher trans-:cis- isomer ratio than is achievable by conventional hydrogenation methods. Hence it is a still further object of the invention to avoid the increased capital and operating costs of the prior art processes mentioned above which require the use of extreme hydrogenation conditions or a separate isomerisation step. It is also an object of the present invention to provide a process wherein a mixture of cis- and trans- isomers of dimethyl 1,4-cyclohexanedicarboxylate is reacted rapidly with high conversion and high selectivity to a mixture of cis- and trans-isomers of 1,4-cyclohexanedimethanol.

According to the present invention there is provided a process for the production of a hydroxylic compound selected from alcohols and diols by hydrogenation of a corresponding hydrogenatable material selected from monoesters of carboxylic acids, monoesters of dicarboxylic acids, diesters of dicarboxylic acids, lactones, and mixtures of two or more thereof which comprises:

(a) providing a hydrogenation zone containing a charge of a granular heterogeneous ester hydrogenation catalyst;

(b) supplying to the hydrogenation zone a vaporous feed stream containing hydrogen and a hydrogenatable material selected from monoesters of carboxylic acids, monoesters of dicarboxylic acids, diesters of dicarboxylic acids, lactones, and mixtures of two or more thereof, at an inlet temperature which is above the dew point of the mixture;

(c) maintaining the hydrogenation zone under temperature and pressure conditions which are conducive to effecting hydrogenation of esters;

(d) recovering from the hydrogenation zone a two phase product stream containing a hydroxylic compound selected from alcohols and diols at an exit temperature which is below its dew point.

The invention is based upon the surprising discovery that, when hydrogenating dimethyl 1,4-cyclohexanedicarboxylate, not only is the conversion of the starting material, i.e. dimethyl 1,4-cyclohexanedicarboxylate, to the product, i.e. 1,4-cyclohexanedimethanol, extremely rapid under the hydrogenation conditions used, requiring only a matter of a few seconds for substantially complete conversion to occur, but also the isomerisation of 1,4-cyclohexanedimethanol that occurs in passage through the hydrogenation zone is comparably rapid. This is a surprising finding since two separate reactions are involved. Thus, for example, when the hydrogenatable material comprises a cis-rich dimethyl 1,4-cyclohexanedicarboxylate having a trans-:cis- isomer ratio of less than about 1:1, e.g. about 0.5:1 to about 0.6:1, a high trans-:cis- 1,4-cyclohexanedimethanol ratio, typically greater than about 2.0:1 up to about 3.84:1, as well as essentially complete conversion of dialkyl 1,4-cyclohexanedicarboxylate to 1,4-cyclohexanedimethanol, can be achieved by using a residence time of less than about a minute of the reaction mixture in the hydrogenation zone, typically in the range of from about 2 to about 15 seconds. This residence time is in stark contrast to the extended residence times recommended in the prior art, such as the 40 to 50 minutes residence time used in Example 1 of US-A-3334149.

The process of the invention is operated using vaporous feed conditions with the feed stream being supplied to the hydrogenation zone in essentially liquid free vaporous form. Hence the feed stream is supplied to the hydrogenation zone at an inlet temperature which is just above the dew point of the mixture. However, when using dimethyl 1,4-cyclohexanedicarboxylate as starting material the product, 1,4-cyclohexanedimethanol, is less volatile than the starting material, dimethyl 1,4-cyclohexanedicarboxylate. Since the feed temperature of the feed stream is above but sufficiently close to its dew point, condensation of a 1,4-cyclohexanedimethanol-rich liquid can occur on the catalyst. Such condensation of a 1,4-cyclohexanedimethanol-rich liquid on the catalyst is not deleterious in the process of the invention because the heat of hydrogenation of any dimethyl 1,4-cyclohexanedicarboxylate present in the 1,4-cyclohexanedimethanol-rich liquid can be dissipated by the heat sink effect of the 1,4-cyclohexanedimethanol. However, it is essential that the feed stream be at a feed temperature above its dew point at the inlet end of the catalyst bed if the advantage of vapour phase feed conditions is to be realised. The use of vapour phase feed conditions in the process of the invention has the advantage that, compared with liquid phase operation of the process, generally lower operating pressures can be used. This generally has a significant and beneficial effect not only on the construction costs but also on the operating costs of the plant.

In the hydrogenation zone the hydrogenatable material undergoes extremely rapid hydrogenation to yield the hydroxylic compound, as exemplified by equation (2) above. For the sake of convenience the description hereafter will largely be confined to consideration of the hydrogenation of dimethyl cyclohexanedicarboxylate to cyclohexanedimethanol. However, it will be appreciated by those skilled in the art that other esters, diesters or lactones can be substituted for dimethyl cyclohexanedicarboxylate in accordance with the teachings of the present invention.

When the hydrogenatable material comprises dimethyl cyclohexanedicarboxylate, an additional isomerisation reaction occurs under the hydrogenation conditions. Hence a hydrogenatable material rich in cis-dimethyl cyclohexanedicarboxylate tends to yield a cyclohexanedimethanol product that has a higher content of the trans-isomer thereof than the trans-content of the starting ester. In the case of hydrogenation of a cis-rich dimethyl 1,4-cyclohexanedicarboxylate we have found that the trans-:cis- isomer ratio of the 1,4-cyclohexanedimethanol present in the product mixture can be as high as approximately 3.84:1. This ratio is significantly higher than the ratio of between 2.57:1 and 3:1 which is reported to be achieved under liquid phase reaction conditions at low conversions.

In a particularly preferred process the dimethyl cyclohexanedicarboxylate is dimethyl 1,4-cyclohexanedicarboxylate and the product stream of step (d) is a 1,4-cyclohexanedimethanol product in which the trans-:cis- isomer ratio is in the range of from about 2:1 up to about 3.84:1, and is more preferably at least about 2.6:1 up to about 3.84:1. The process of the invention thus readily permits the preparation in a single step of a 1,4-cyclohexanedimethanol product in which the trans-:cis- isomer ratio is in excess of about 2:1 up to about 3.84:1, for example from about 2.6:1 to about 2.7:1. It is preferred that this ratio is at least about 2.6:1. The invention permits production in a single step of a 1,4-cyclohexanedimethanol product with a trans-:cis- isomer ratio of from about 3.1:1 up to about 3.84:1, e.g. about 3.2:1 up to about 3.7:1.

The hydrogenatable material supplied to the hydrogenation zone may comprise substantially pure cis-dimethyl cyclohexanedicarboxylate, trans-dimethyl cyclohexanedicarboxylate, or a mixture thereof in any proportion. A typical commercial grade of dimethyl 1,4-cyclohexanedicarboxylate has a molar ratio of the trans-isomer to the cis-isomer in the hydrogenatable material of from about 0.5:1 to about 0.6:1.

Whilst the process is used to advantage for the hydrogenation of dimethyl 1,4-cyclohexanedicarboxylate, it will be understood by those skilled in the art that the process of the invention may be equally well applied to the hydrogenation of any or all of dimethyl 1,2-cyclohexanedicarboxylate, dimethyl 1,3-cyclohexanedicarboxylate or dimethyl 1,4-cyclohexanedicarboxylate, and mixtures of two or more thereof.

Also contemplated for use in the invention are other diesters, e.g. dialkyl (preferably di-($C_1$ to $C_4$ alkyl)) esters of dicarboxylic acids containing from 4 to about 12 carbon atoms, lactones containing from 4 to about 16 carbon atoms, and esters of monocarboxylic acids containing from 8 to about 18 carbon atoms, preferably alkyl esters (e.g. methyl or ethyl esters) of monocarboxylic acids having from about 8 to about 18 carbon atoms. Hence other hydrogenatable materials which can be used in the process of the invention include dialkyl maleates, fumarates, and succinates, for example di-($C_1$ to $C_4$ alkyl) maleates, fumarates, and succinates, which yield butane-1,4-diol, as well as gamma-butyrolactone and epsilon-caprolactam which yield butane-1,4-diol and hexane-1,6-diol respectively. It is also possible to utilise, as hydrogenatable material, dialkyl esters of glutaric acid, adipic acid and azelaic acid, particularly the methyl and ethyl esters thereof, as well as the methyl esters of capric acid, oleic acid, lauric acid, myristic acid, palmitic acid, stearic acid, and mixtures thereof.

A surprising discovery is that the process of the invention can generate 1,4-cyclohexanedimethanol product mixtures whose trans-:cis-isomer ratio is in excess of the ratio that is the normal equilibrium ratio under liquid phase conditions. Thus, although the normal reported trans-:cis- isomer equilibrium ratio, under liquid phase conditions, can under favourable conditions be as high as about 3:1, the present invention enables production from a cis-rich dimethyl 1,4-cyclohexanedicarboxylate of 1,4-cyclohexanedimethanol with a trans-:cis-isomer ratio as high as 3.84:1.

It is also surprising that the process of the invention can be operated for extended periods of up to several months or more, at high selectivity to the desired cyclohexanedimethanol product and at high conversion of the starting dialkyl cyclohexanedicarboxylate, since the prejudice in the art is that copper-containing catalysts would only have a short operating life and low activity at low operating pressure.

In the prior art it is made clear that the hydrogenation of dimethyl 1,4-cyclohexanedicarboxylate (dimethyl hexahydroterephthalate) is liable to give significant quantities of by-products. Thus GB-A-988316 acknowledges the problem caused by formation of unwanted by-products, such as 1-methyl-4-hydroxymethylcyclohexane. It is surprising to find that the process of the invention can be operated so that, despite the presence of a very large excess of hydrogen and the use of a very large vapour pressure of hydrogen compared to the relatively low vapour pressure of dimethyl cyclohexanedicarboxylate, the reaction proceeds rapidly with a very high conversion of dimethyl cyclohexanedicarboxylate to the desired product, i.e. cyclohexanedimethanol, but yet with a very high selectivity to that product and therefore with a very low yield of by-products. Thus under favourable conditions the conversion of dimethyl cyclohexanedicarboxylate to cyclohexanedimethanol can be as high as 98 mole % or higher with a selectivity to cyclohexanedimethanol of greater than 96 mole %. In addition it surprising to find that it is possible, under suitable reaction conditions, to convert a starting ester (dimethyl 1,4-cyclohexanedicarboxylate) that has a trans-:cis- isomer ratio less than 1:1 in a single step to a cyclohexanedimethanol product with a trans-:cis- isomer ratio that is greater than 1:1 and normally in the range of from about 2.6:1 up to as high as about 3.84:1, a value that is much higher than the highest reported equilibrium trans-:cis- isomer ratio that is disclosed in the prior art. It is further surprising to find that this can be accomplished at relatively low operating temperatures and pressures.

In a commercial plant the process will normally be operated on a continuous basis. It may be preferred to employ at least two hydrogenation zones, each containing a charge of a heterogeneous ester hydrogenation catalyst, connected in parallel. Each of these zones is capable of independent isolation from the supply of vaporous feedstock mixture. Hence an isolated zone may be subjected to conditions substantially different from those prevailing in the remaining zone or zones, for example, whereunder the catalyst charge therein may be reactivated or replaced whilst the process of the invention is continued in the remaining zone or zones. This arrangement also permits operation under the conditions taught in WO-A-91/01961. In this case two hydrogenation reactors connected in parallel are used. In a first phase of operation with a fresh charge of catalyst one only of the reactors is used, the other one being in standby mode with the catalyst bathed in hydrogen. After a period of operation over which the catalyst activity may decline somewhat the second reactor is used, whilst the first one is placed in standby condition. After a further period of operation both reactors are used in parallel until the time comes to replace the entire catalyst charge.

The process of the invention is normally operated at a feed temperature of at least about 150° C. and no higher than about 350° C. The hydrogenation temperature is preferably in the range of from about 150° C. to about 300° C., most preferably from about 200° C. to about 260° C.

The feed pressure typically is in the range of from about 150 psia (about 10.34 bar) up to about 2000 psia (about 137.90 bar). However, the benefits and advantages of the present low pressure, process utilising vapour phase feed conditions are best realised by carrying out the process at a pressure of from about 450 psia (about 31.03 bar) up to about 1000 psia (about 68.95 bar).

The process requires that the vaporous feed stream is above its dew point at the inlet end of the or each hydrogenation zone so that the dimethyl cyclohexanedicarboxylate or other hydrogenatable material is present in the vapour phase at the inlet end of the or each catalyst bed. This means that the composition of the vaporous feed mixture must be controlled so that, under the selected operating conditions, the temperature of the mixture at the inlet end of the or each catalyst bed is always above its dew point at the operating pressure. By the term "dew point" is meant that temperature at which a mixture of gases and vapours just deposits a fog or film of liquid. This dew point liquid will normally contain all the condensable components of the vapour phase, as well as dissolved gases, in concentrations that satisfy the usual vapour/liquid criteria. Typically the feed temperature of the vaporous feed mixture to the hydrogenation zone is from about 5° C. up to about 10° C. or more above, e.g. up to about 20° C. above, its dew point at the operating pressure.

One reason for requiring that the hydrogenatable material shall be in the vapour phase in the feed stream is that hydrogenation reactions are usually exothermic. By using vapour phase conditions in the feed stream the risk of droplets of a liquid phase rich in hydroxylic compound contacting the catalyst with a consequential risk of development of "hot spots" and formation of "fines" due to explosive localised vaporisation of liquid within the pores of the catalyst are minimised. On the other hand condensation of a liquid rich in hydroxylic compound can be tolerated since the hydroxylic compound is essentially inert and its presence helps to reduce the development of "hot spots" since its heat of vaporisation will help to dissipate any excessive localised heat of hydrogenation.

A convenient method of forming a vaporous mixture for use in the process of the invention is to spray the hydrogenatable material or a solution thereof into a stream of hot hydrogen-containing gas so as to form a saturated or partially saturated vaporous mixture. Alternatively such a vapour mixture can be obtained by bubbling a hot hydrogen-containing gas through a body of the hydrogenatable material or a solution thereof. If a saturated vapour mixture is formed it should then be heated further or diluted with more hot gas so as to produce a partially saturated vaporous mixture prior to contact with the catalyst.

The hydrogen-containing gas used in the process may comprise fresh make-up gas or a mixture of make-up gas and recycle gas. The make-up gas can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired. If gas recycle is utilised in the process then the recycle gas will normally contain minor amounts of one or more products of the hydrogenation reaction which have not been fully condensed in the product recovery stage downstream from the hydrogenation zone. For example, in the hydrogenation of dimethyl cyclohexanedicarboxylate using gas recycle, the gas recycle stream will contain minor amounts of methanol.

In order to maintain the vaporous feed stream above its dew point at the inlet end of the or each catalyst bed at the operating pressure the hydrogen-containing gas:-hydrogenatable material molar ratio is desirably at least about 10:1 up to about 8000:1, preferably in the range of from about 200:1 to about 1000:1. It is, however, surprising to find that, when using dimethyl 1,4-cyclohexanedicarboxylate as the hydrogenatable material, it is not necessary that the vaporous mixture in contact with all parts of the or each catalyst bed should be so far above its dew point as to prevent condensation of a 1,4-cyclohexanedimethanol-rich liquid. (1,4-Cyclohexanedimethanol is less volatile than the ester starting material, dimethyl 1,4-cyclohexanedicarboxylate).

At the inlet end of the or each bed of hydrogenation catalyst, the vaporous stream contains, in addition to the gas or gases including hydrogen, the hydrogenatable material as the main component of the condensable (liquefiable) fraction, the other condensable components being any hydroxylic compound present in any recycle gas stream. As the reaction mixture passes through the hydrogenation catalyst so the proportion of hydrogenatable material in the condensable fraction falls accompanied by a corresponding increase in the amount of hydroxylic compound. Near the exit end of the bed the amount of hydrogenatable material, e.g. dimethyl cyclohexanedicarboxylate, may have fallen to a very low level, e.g. about 0.5 mole % or less. Since the exothermic heat of hydrogenation of the residual amount of dimethyl cyclohexanedicarboxylate is relatively small, the risk of damage to the catalyst is very small. Hence condensation of liquefiable materials, which mainly consist of the product, e.g. 1,4-cyclohexanedimethanol, towards the exit end of the catalyst bed can be permitted. The benefit for the plant operator is that, because 1,4-cyclohexanedimethanol is less volatile than dimethyl 1,4-cyclohexanedicarboxylate, it is not necessary to use such a high hydrogen-containing gas:-dimethyl 1,4-cyclohexanedicarboxylate molar ratio in the vaporous feed stream that condensation of cyclohexanedimethanol is prevented. Because the plant operator can use a reduced gas:dimethyl 1,4-cyclohexanedicarboxylate ratio compared with that necessary for a true vapour phase process, in which both product and starting material are maintained in the vapour phase throughout the catalyst bed, it is not necessary to circulate so much hydrogen-containing gas. Hence the operating cost of the plant can be reduced and heat losses can be minimised since less circulating gas is being heated and cooled.

Although the process of the invention is operated with the feed stream in the vapour phase, it is convenient to express the feed rate of the hydrogenatable material to the hydrogenation zone as a space velocity through the hydrogenation catalyst and to express that space velocity as a liquid hourly space velocity. Hence it is convenient to express the feed rate in terms of the ratio of the liquid feed rate of the hydrogenatable material to the vaporisation zone to the volume of the hydrogenation catalyst. Thus the equivalent liquid hourly space velocity of the hydrogenatable material through the hydrogenation catalyst is preferably from about 0.05 to about 4.0 $h^{-1}$. In other words it is preferred to feed the liquid hydrogenatable material to the vaporisation zone at a rate which is equivalent to, per unit volume of catalyst, from about 0.05 to about 4.0 unit volumes of hydrogenatable material per hour (i.e. about 0.05 to about 4.0 $m^3 h^{-1}$ per $m^3$ of catalyst). Even more preferably the liquid hourly space velocity is from about 0.1 $h^{-1}$ to about 1.0 $h^{-1}$. If the hydrogenatable material is a solid at ambient temperatures, as is the case, for example, with trans-dimethyl 1,4-cyclohexanedicarboxylate, then it may be necessary to heat it sufficiently to melt it or to dissolve it in a suitable inert solvent, in which latter case the solvent is ignored for the purpose of measuring the liquid hourly space velocity.

It will be readily apparent to those skilled in the art that the rate of passage of the vaporous feed stream through the hydrogenation zone will depend upon the feed rate of the unsaturated organic compound to the vaporisation zone and upon the hydrogen-containing gas:hydrogenatable material molar ratio.

In the process of the invention the product stream is recovered from the downstream end of the hydrogenation zone in step (d) as a two phase mixture, i.e. as a mixture of vapour-containing gas and liquid. Typically this mixture exits the catalyst bed or the final catalyst bed at an exit temperature which is from about 1° C. to about 20° C., but preferably not more than about 1° C. to about 10° C., below its dew point at the operating pressure.

Dimethyl 1,4-cyclohexane-dicarboxylate is commercially available as high purity dimethyl 1,4-cyclohexanedicarboxylate, technical grade dimethyl 1,4-cyclohexanedicarboxylate, cis-dimethyl 1,4-cyclohexanedicarboxylate, or trans-dimethyl 1,4-cyclohexanedicarboxylate. The preferred feedstock for the process of the invention is the technical grade dimethyl 1,4-cyclohexanedi-carboxylate, as the high purity, cis-, and trans- grades of dimethyl 1,4-cyclohexanedicarboxylate require additional purification stages in the course of their production.

The granular catalyst used in the process of the invention may be any catalyst capable of catalysing hydrogenation or hydrogenolysis of an ester to the corresponding alcohol or mixture of alcohols. It may be formed into any suitable shape, e.g. pellets, rings or saddles.

Typical ester hydrogenation catalysts include copper-containing catalysts and Group VIII metal-containing catalysts. Examples of suitable copper-containing catalysts include copper-on-alumina catalysts, reduced copper oxide/zinc oxide catalysts, with or without a promoter, manganese promoted copper catalysts, and reduced copper chromite catalysts, with or without a promoter, while suitable Group VIII metal-containing catalysts include platinum catalysts and palladium catalysts. Suitable copper oxide/zinc oxide catalyst precursors include CuO/ZnO mixtures wherein the Cu:Zn weight ratio ranges from about 0.4:1 to about 2:1. An example is the catalyst precursor bearing the designation DRD 92/71. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor available under the designation DRD 92/92. Suitable copper chromite catalyst precursors include those wherein the Cu:Cr weight ratio ranges from about 0.1:1 to about 4:1, preferably from about 0.5:1 to about 4:1. Catalyst precursors of this type are the precursors available under the designation DRD 89/21 or under the designation PG 85/1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. An example is the catalyst precursor DRD 92/89.

All of the above mentioned catalysts available under the general designations DRD or PG can be obtained from Davy Research and Development Limited, P.O. Box 37, Bowesfield Lane, Stockton-on-Tees, Cleveland TS18 3HA, England.

Other catalysts which can be considered for use include Pd/ZnO catalysts of the type mentioned by P. S. Wehner and B. L. Gustafson in Journal of Catalysis 136, 420–426 (1992), supported palladium/zinc catalysts of the type disclosed in US-A-4837368 and US-A-5185476, and chemically mixed copper-titanium oxides of the type disclosed in US-A4929777.

Further catalysts of interest for use in the process of the invention include the rhodium/tin catalysts reported in A. El Mansour, J. P. Candy, J. P. Bournonville, O. A. Ferrehi, and J. M Basset, Angew. Chem. 101, 360 (1989).

Any recognised supporting medium may be used to provide physical support for the catalyst used in the process of the invention. This support can be provided by materials such as zinc oxide, alumina, silica, aluminasilica, silicon carbide, zirconia, titania, carbon, a zeolite, or any suitable combination thereof.

The catalysts that are particularly preferred for use in the process of the invention are the copper-containing catalysts, particularly reduced copper chromite, with or without a promoter, and manganese promoted copper catalysts.

According to one preferred procedure the process of the invention is carried out using at least two hydrogenation reactors connected in parallel, each zone containing a respective charge of the hydrogenation catalyst. The vaporous feedstock mixture may, in a first phase of operation with a fresh catalyst charge, be supplied to one reactor only whilst the second reactor is in standby mode and then, in a second phase of operation, be supplied to the second reactor whilst the first reactor is in standby mode. In each of these first two phases the initially fresh catalyst charge in the respective reactor will become somewhat deactivated. In a third phase of operation the vaporous feed mixture is supplied to both reactors simultaneously, as taught in WO-A-91/01961. In this way the effective life of the total catalyst charge can be extended.

It is also contemplated to use a hydrogenation zone which comprises two or more hydrogenation reactors connected in series.

The or each hydrogenation zone may comprise a shell-and-tube reactor which may be operated under isothermal, or near isothermal, conditions with the catalyst in the tubes and the coolant in the shell or vice versa. Usually, however, it will be preferred to use adiabatic reactors since these are cheaper to construct and install than shell-and-tube reactors. Such an adiabatic reactor may contain a single charge of a hydrogenation catalyst or may contain two or more beds of catalyst, or beds of different hydrogenation catalysts. If desired, external or internal inter-bed heat exchangers may be provided in order to adjust the inlet temperature to one or more beds of catalyst downstream from the inlet to the adiabatic hydrogenation reactor.

Figure 1:
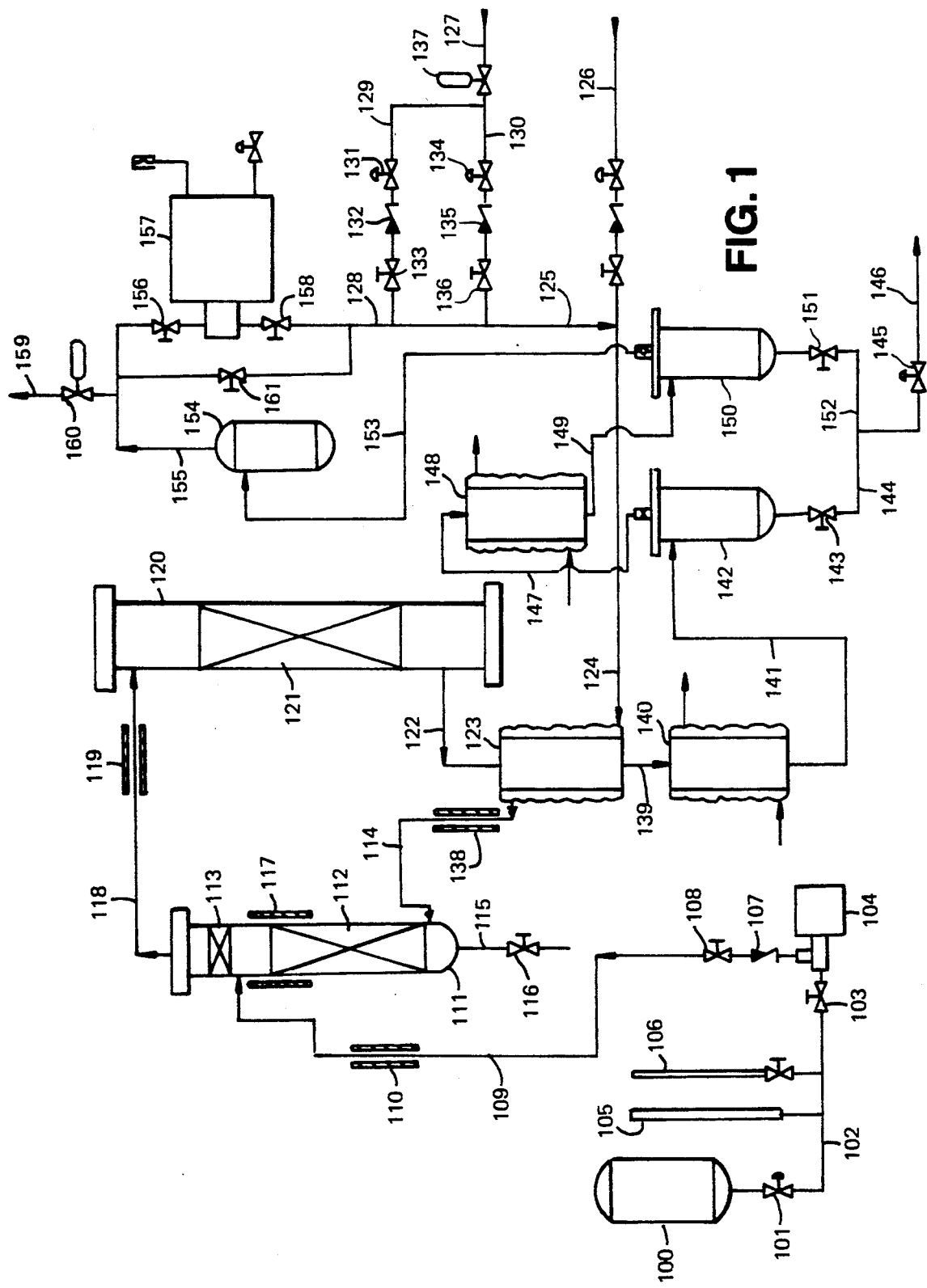
FIG. 1 is a simplified flow diagram of an experimental apparatus for production of 1,4-cyclohexanedimethanol in a single hydrogenation zone by hydrogenation of dimethyl 1,4-cyclohexanedicarboxylate.

The invention is further described with reference to the following Examples. The composition of catalyst A used in the Examples is listed in Table I. The oxygen content of the catalyst has been excluded from the analysis.

TABLE I

| Catalyst | Composition wt % | | | | | | Surface area m²/g | Density g/cm³ | Pore volume mm³/g |
|---|---|---|---|---|---|---|---|---|---|
| | Cu | Cr | Zn | Mn | Ba | Al | | | |
| A DRD 92/89 | 41.1 | 0.26 | <0.01 | 6.4 | <0.01 | 20.4 | 47.1 | 1.452 | 211 |

EXAMPLE 1 (COMPARATIVE EXAMPLE)

The hydrogenation of a technical grade of dimethyl 1,4-cyclohexanedicarboxylate was investigated using the experimental apparatus illustrated in FIG. 1.

The composition of the technical grade feed was: 34.15 wt% trans-dimethyl 1,4-cyclohexanedicarboxylate, 62.00 wt% cis-dimethyl 1,4-cyclohexanedicarboxylate, 1.07 wt% methyl hydrogen cyclohexane-1,4-dicarboxylate of formula

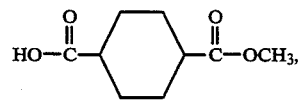

0.05 wt% water and 2.73 wt% of high boiling impurities including di-4-hydroxymethylcyclohexyl methyl ether.

In a commercial plant, hydrogen gas is separated from the hydrogenation product and is advantageously recycled through the hydrogenation zone. The hydrogen recycle stream will contain a quantity of methanol vapour produced by the hydrogenation of dimethyl 1,4-cyclohexanedicarboxylate. Hence, the vaporous feed stream supplied to the hydrogenation zone in a commercial plant will generally contain methanol in addition to hydrogen and an unsaturated organic compound. In order that the experimental rig described hereinbelow should accurately predict the likely results obtained during commercial operation, the liquid feed supplied to the vaporiser was supplemented by a quantity of liquid methanol corresponding to the quantity of methanol which would be contained in the recycle hydrogen stream in a commercial plant. Although hydrogen is recycled in the experimental rig described hereinbelow, the quantity of methanol contained within the recycle hydrogen stream is proportionately less than would be contained in a corresponding commercial recycle stream. This difference arises because the recycle gas in the experimental rig is cooled substantially below the temperature to which it would be desirably cooled in a commercial plant. More methanol is therefore "knocked out" of the experimental recycle hydrogen stream. This discrepancy between the experimental rig and a commercial plant is necessitated by the delicacy of the equipment, particularly the analytical equipment, used in the experimental rig. In this Example and in all succeeding Examples, methanol is added to the experimental liquid feed in a quantity which is substantially equal to the proportionate quantity of methanol which would be present in the experimental recycle stream if the rig were operated under commercial conditions minus the quantity of methanol actually present in the experimental recycle hydrogen stream. In the Examples, all parameters such as conversion rates and hourly space velocities are calculated on a methanol free basis.

The experimental apparatus is illustrated in FIG. 1. An approximately 70 wt% solution of the technical grade of dimethyl 1,4-cyclohexanedicarboxylate in methanol is fed from reservoir 100 by way of valve 101, line 102 and valve 103 to liquid feed pump 104. Burette 105 provides a buffer supply whilst burette 106 is fitted with a liquid level controller (not shown) that controls valve 101 so as to ensure that liquid feed is supplied from reservoir 100 to liquid feed pump 104 at a constant head. The liquid feed is pumped through non-return valve 107 and isolation valve 108 into line 109, which can be heated by electrical heating tape 110, before the heated liquid enters the upper part of an insulated vaporiser vessel 111 above a bed of 6 mm × 6 mm glass rings 112. A stainless steel demister pad 113 is fitted at the top end of the vaporiser vessel 111. A stream of hot hydrogen-containing gas is supplied to the bottom of vaporiser 111 in line 114. A liquid drain line 115 fitted with a drain valve 116 enables withdrawal of any unvaporised liquid feed material (e.g. "heavies") from the base of the vaporiser vessel 111. The vaporisation of the liquid feed supplied to the vaporiser vessel 111 is assisted by heating tape 117. A saturated vaporous mixture comprising dimethyl 1,4-cyclohexanedicarboxylate and hydrogen is recovered in line 118 from the top of vaporiser vessel 111. The vaporous mixture is heated by heating tape 119 in order to raise its temperature above the dew point of the mixture prior to entering the top end of hydrogenation reactor 120 which contains a bed of 300 ml (428.1 g) of a pelleted copper chromite hydrogenation catalyst 121. The catalyst was catalyst A of Table I. Glass rings are packed in reactor 120 above and below the catalyst bed 121. The vaporous mixture passes downward through catalyst bed 121 where conversion of dimethyl 1,4-cyclohexanedicarboxylate to 1,4-cyclohexanedimethanol occurs under adiabatic conditions. Adiabaticity is maintained by electrical heating tapes (not shown) embedded within insulating material around reactor 120 under the control of appropriately positioned thermocouples (not shown). The overall reaction is mildly exothermic with a general increase in catalyst bed temperature of approximately 1° to 2° C. The hydrogenation product mixture exits the hydrogenation reactor 120 in line 122 and is passed through heat exchanger 123 which simultaneously cools the hydrogenation product mixture and heats a supply of hydrogen-containing gas from line 124. Condensation of the bulk of the 1,4-cyclohexanedimethanol in line 122 occurs in heat exchanger 123. The gas in line 124 comprises hydrogen-containing gas from line 125 and, optionally, an inert gas or a mixture of inert gases such as nitrogen, argon or methane supplied in line 126. The gas in line 125 comprises make-up hydrogen supplied in line 127 and recycle hydrogen supplied in line 128. Make-up hydrogen in line 127 may be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passes on in line 114 and is heated further by electrical heating tape 138 for supply to the vaporiser vessel 111.

The cooled hydrogenation product from heat exchanger 123 passes on through line 139 to be cooled further in cooler 140 to a temperature near ambient temperature. The liquid/vapour mixture from cooler 140 passes on in line 141 to a first knockout pot 142 where liquid hydrogenation product is collected for eventual supply by means of valve 143, line 144 and line 145 to product line 146. A vaporous mixture comprising hydrogen and uncondensed methanol exits the top of knockout pot 142 in line 147 and is further cooled to a temperature of 10° C. in cooler 148. The further cooled liquid/vapour mixture from cooler 148 is supplied via line 149 to a second knockout pot 150 wherein condensed methanol is collected for eventual supply through valve 151 and line 152 to product line 146. The gas and uncondensed materials from knockout pot 150 are supplied via line 153 through suction pot 154 into line 155 and then through valve 156 to gas recycle compressor 157. Gas is recycled through valve 158 lines 128, 125, 124 and 114 to vaporiser 111. In order to control the concentration of inert gases, such as nitrogen, in the circulating gas a purge gas stream may be bled from the system in line 159 under the control of valve 160.

Reference numeral 161 indicates a bypass valve.

At start up of the apparatus the charge of catalyst was placed in reactor 120 which was then purged with nitrogen. The catalyst charge was then reduced by a method similar to that taught in EP-A-0301853.

Technical dimethyl 1,4-cyclohexanedicarboxylate, appropriately diluted with methanol, was then pumped to the vaporiser 111 at a rate of 120 ml/h corresponding to a liquid hourly space velocity of 0.4 h$^{-1}$. The gas:-dimethyl 1,4-cyclohexanedicarboxylate mole ratio in the vapour mixture was 710:1. The reactor 120 was maintained at a temperature of 220° C. and a pressure of 900 psia (62.05 bar). The hydrogenation zone was therefore operated under conditions which permitted some condensation of the 1,4-cyclohexanedimethanol product. The temperature in the hydrogenation zone was 13.0° C. above the dew point of the reaction product mixture at the exit end from the catalyst bed.

The liquid in line 146 was analysed periodically by capillary gas chromatography using a 15m long, 0.32 mm internal diameter fused silica column coated internally with a 0.25 μm film of DB wax, a helium flow rate of 2 ml/minute with a gas feed split ratio of 100:1 and a flame ionisation detector. The instrument was fitted with a chart recorder having a peak integrator and was calibrated using a commercially available sample of dimethyl 1,4-cyclohexanedicarboxylate of known composition. The exit gas was also sampled and analysed by gas chromatography using the same technique. The identities of the peaks were confirmed by comparison of the retention times observed with those of authentic specimens of the materials in question and by mass spectroscopy. Included amongst the compounds detected in the reaction mixture were 1,4-cyclohexanedimethanol, dimethyl 1,4-cyclohexanedicarboxylate, 4-methoxymethyl cyclohexanemethanol, di-(4-methoxymethylcyclohexylmethyl) ether, and methanol. From the results obtained it was demonstrated that dimethyl 1,4-cyclohexanedicarboxylate can be converted in excess of 99%, with a selectivity to 1,4-cyclohexanedimethanol of approximately 98.9% being obtained, the balance being minor by-products. After making due allowance for the methanol present in the feed solution of dimethyl 1,4-cyclohexanedicarboxylate from reservoir 100, 2 moles of methanol were detected for every 1 mole of dimethyl 1,4-cyclohexanedicarboxylate converted in accordance with the stoichiometry of the hydrogenation reaction. The results are listed in Table II below, together with the results from the succeeding Examples 2 to 4.

EXAMPLE 2

Using a similar procedure to that described in Example 1 and the same feed solution and catalyst charge, a further run was carried out with a much lower hydrogen-containing gas:dimethyl 1,4-cyclohexanedicarboxylate molar ratio in the vaporous feed stream. Hence in this case the reaction mixture at the exit from the catalyst bed was 4.2° C. below its dew point. The results are summarised in Table II. Even though the catalyst bed was wetted, no significant drop in conversion occurred upon moving from wholly vapour phase conditions to the conditions of the process of the invention, nor was there a significant change in selectivity to 1,4-cyclohexanedimethanol.

EXAMPLES 3 AND 4

The same procedure was used as for Example 2. In both cases the reaction mixture exiting the catalyst bed was below its dew point. Hence the catalyst bed was wetted. The operating conditions and results are listed in Table II.

EXAMPLES 5 AND 6

The general procedure of Examples 2 to 4 is repeated using, in place of dimethyl 1,4-cyclohexanedicarboxylate, dimethyl 1,2-cyclohexanedicarboxylate and dimethyl 1,3-cyclohexanedicarboxylate respectively. Similar results are obtained.

EXAMPLES 7 TO 15

The general procedure of Examples 2 to 4 is repeated using in place of dimethyl 1,4-cyclohexanedicarboxylate one of the following diesters:
(i) dimethyl maleate;
(ii) dimethyl fumarate;
(iii) diethyl maleate;
(iv) diethyl succinate;
(v) dimethyl succinate;
(vi) dimethyl glutarate;
(vii) dimethyl adipate;
(viii) dimethyl pimelate; or
(ix) dimethyl azelate.

Similar results are observed to those reported for Examples 2 to 4.

EXAMPLES 16 TO 22

The general procedure of Examples 2 to 4 is repeated using one of the following esters:
(i) methyl caprate;
(ii) methyl oleate;
(iii) methyl laurate;
(iv) methyl myristate;
(v) methyl palmitate;
(vi) methyl stearate; or
(vii) a mixture of methyl esters obtained by hydrolysis of coconut oil followed by "topping and tailing" so as to obtain a mixture of fatty acids of defined boiling range.

Good results are obtained in each case.

We claim:

1. A process for the production of alcohols and diols by hydrogenation of a corresponding hydrogenatable material selected from monoesters of carboxylic acids, monoesters of dicarboxylic acids, diesters of dicarboxylic acids, lactones, and mixtures of two or more thereof which comprises:
  (a) providing a hydrogenation zone containing a charge of a granular heterogeneous copper-containing ester hydrogenation catalyst;

TABLE II

| Example No. | Pressure psia (bar) | Inlet Temp. °C. | Gas:DMCD mol ratio | ADP °C. | LHSV $h^{-1}$ | DMCD conversion mol % | CHDM trans-:cis- ratio | Selectivity mol % | | | |
|---|---|---|---|---|---|---|---|---|---|---|---|
| | | | | | | | | CHDM | BYPR | METH | DETH |
| 1 | 900 (62.05) | 220 | 710 | +13.0 | 0.40 | 99.82 | 3.34 | 98.91 | 0.65 | 0.25 | 0.19 |
| 2 | 900 (62.05) | 220 | 383 | −4.2 | 0.40 | 99.79 | 3.48 | 98.26 | 0.94 | 0.67 | 0.13 |
| 3 | 900 (62.05) | 220 | 351 | −5.7 | 0.40 | 99.87 | 3.28 | 98.15 | 1.47 | 0.17 | 0.21 |
| 4 | 900 (62.05) | 220 | 248 | −16.2 | 0.40 | 99.93 | 3.26 | 98.23 | 1.50 | 0.15 | 0.12 |

Notes to TABLE II:
DMCD = dimethyl 1,4-cyclohexanedicarboxylate
ADP = approach to dew point of the reaction product mixture at the exit end from the catalyst bed
LHSV = liquid hourly space velocity
CHDM = cyclohexanedimethanol
BYPR = miscellaneous byproducts
METH = 4-methoxymethyl cyclohexanemethanol
DETH = di-4-hydroxymethylcyclohexylmethyl ether
Gas = hydrogen-containing gas containing more than 98% v/v hydrogen (b) supplying to the hydrogenation zone a vaporous feed stream containing hydrogen and a hydrogenatable material selected from $C_1$ to $C_4$ alkyl monoesters of monocarboxylic acids having from 8 to about 18 carbon atoms, di-($C_1$ to $C_4$ alkyl diesters of dicarboxylic acids containing from 4 to about 12 carbon atoms, gamma-butyrolactone, and mixtures of two or more thereof, at an inlet temperature which is above the dew point of the mixture;

(c) maintaining the hydrogenation zone at a temperature of at least about 150° C. up to about 350° C. and pressure of from about 150 psia up to about 2000 psia;

(d) recovering from the hydrogenation zone a two phase product stream containing an alcohol or a diol at an exit temperature which is below its dew point.

2. A process according to claim 1, in which the product stream is recovered from the hydrogenation zone at an exit temperature which is from about 1° C. to about 20° C. below its dew point.

3. A process according to claim 1, in which the hydrogenatable material comprises dimethyl cyclohexanedicarboxylate and wherein the product stream comprises cyclohexanedimethanol.

4. A process according to claim 3, in which the dimethyl cyclohexanedicarboxylate is dimethyl 1,4-cyclohexanedicarboxylate and wherein the product stream comprises 1,4-cyclohexanedimethanol.

5. A process according to any one of claim 4, in which the hydrogenatable material comprises dimethyl 1,4-cyclohexanedicarboxylate and in which the flow rate is adjusted to yield a 1,4-cyclohexanedimethanol product having a trans-:cis- isomer ratio of from about 2.6:1 to about 2.7:1.

6. A process according to claim 3, in which the hydrogenatable material comprises dimethyl 1,3-cyclohexanedicarboxylate and wherein the product stream comprises 1,3 cyclohexanedimethanol.

7. A process according to claim 3, in which the hydrogenatable material comprises dimethyl 1,2-cyclohexanedicarboxylate and wherein the product stream comprises 1,2-cyclohexanedimethanol.

8. A process according to claim 1, in which the hydrogenatable material comprises a diester selected from di-($C_1$ to $C_4$ alkyl dialkyl esters of a $C_4$ dicarboxylic acid selected from maleic acid, fumaric acid, succinic acid, and mixtures of two or more thereof.

9. A process according to claim 8, in which the diester comprises dimethyl or diethyl maleate.

10. A process according to claim 1, in which the hydrogenatable material comprises a $C_1$ to $C_4$ alkyl monoester of a $C_8$ to $C_{18}$ fatty acid.

11. A process according to claim 5, in which the hydrogen-containing gas:hydrogenatable material mole ratio in the vaporous mixture is in the range of from about 200:1 to about 1000:1.

12. A process according to claim 11, in which the feed temperature to the hydrogenation zone is in the range of from about 150° C. to about 300° C.

13. A process according to claim 12, in which the feed temperature to the hydrogenation zone is in the range of from about 200° C. to about 260° C.

14. A process according to claim 12, in which the feed pressure in the hydrogenation zone is in the range of from about 450 psia (about 31.03 bar) to about 1000 psia (about 68.95 bar).

15. A process according to claim 14, in which the catalyst is selected from reduced manganese promoted copper catalysts, reduced copper chromite catalysts, reduced promoted copper chromite catalysts, and chemically mixed copper-titanium catalysts.

16. A process according to claim 15, in which the catalyst is selected from the reduced forms of copper chromite, promoted copper chromite, and manganese promoted copper catalysts.

17. A process according to claim 15, in which the catalyst comprises not more than about 15% by weight of at least one promoter selected from barium, manganese, and mixtures thereof.

18. A process according to claim 1, in which the hydrogenatable material is supplied at a rate corresponding to a liquid hourly space velocity of from about 0.05 to about 4.0 $h^{-1}$.

* * * * *